(12) United States Patent
Jones et al.

(10) Patent No.: US 6,723,108 B1
(45) Date of Patent: Apr. 20, 2004

(54) FOAM MATRIX EMBOLIZATION DEVICE

(75) Inventors: Donald K. Jones, Lauderhill, FL (US); Vladimir Mitelberg, Aventura, FL (US)

(73) Assignee: Cordis Neurovascular, Inc, Miami Lakes, FL (US)

( * ) Notice: Subject to any disclaimer, the term of this patent is extended or adjusted under 35 U.S.C. 154(b) by 223 days.

(21) Appl. No.: 09/663,768

(22) Filed: Sep. 18, 2000

(51) Int. Cl.[7] ............................................... A61B 17/08
(52) U.S. Cl. ........................ 606/151; 606/213; 606/194
(58) Field of Search ................................. 606/200, 213, 606/214, 191, 194, 195, 198, 151, 108

(56) References Cited

U.S. PATENT DOCUMENTS

| | | | |
|---|---|---|---|
| 4,890,612 A | * 1/1990 | Kensey | 606/213 |
| 5,061,274 A | * 10/1991 | Kensey | 606/213 |
| 5,382,259 A | 1/1995 | Phelps et al. | |
| 5,690,671 A | 11/1997 | McGurk et al. | |
| 5,749,894 A | 5/1998 | Engelson | |
| 5,776,184 A | 7/1998 | Tuch | |
| 5,823,198 A | * 10/1998 | Jones et al. | 128/899 |
| 5,833,705 A | 11/1998 | Ken et al. | |
| 5,853,418 A | 12/1998 | Ken et al. | |
| 5,891,192 A | 4/1999 | Murayama et al. | |
| 5,891,558 A | 4/1999 | Bell et al. | |
| 5,895,407 A | 4/1999 | Jayaraman | |
| 5,904,703 A | * 5/1999 | Gilson | 606/213 |
| 6,015,424 A | * 1/2000 | Rosenbluth et al. | 606/200 |
| 6,113,629 A | * 9/2000 | Ken | 606/213 |
| 6,159,165 A | * 12/2000 | Ferrera et al. | 606/194 |
| 6,165,193 A | 12/2000 | Greene, Jr. et al. | |
| 6,238,403 B1 | 5/2001 | Greene, Jr. et al. | |
| 6,245,090 B1 | * 6/2001 | Gilson et al. | 606/213 |
| 6,299,619 B1 | * 10/2001 | Greene et al. | 606/108 |
| 6,375,669 B1 | * 4/2002 | Rosenbluth et al. | 606/200 |

FOREIGN PATENT DOCUMENTS

| | | |
|---|---|---|
| DD | A1 233 303 | 12/1984 |
| WO | A1 WO 94/06460 | 3/1994 |
| WO | A1 WO 99/23954 | 5/1999 |

\* cited by examiner

*Primary Examiner*—Michael J. Milano
*Assistant Examiner*—Jessica R Baxter
(74) *Attorney, Agent, or Firm*—Henry W. Collins

(57) ABSTRACT

The present invention relates to a medical device for placement at a predetermined location within a passageway of the human body, and more particularly, relates to a flexible expandable embolization device which may be delivered by a catheter to a pre-selected position within a blood vessel to thereby embolize a blood vessel or a blood vessel defect, such as an aneurysm or fistula.

42 Claims, 2 Drawing Sheets

FOAM MATRIX EMBOLIZATION DEVICE

BACKGROUND OF THE INVENTION

1. Field of the Invention

The present invention relates to a medical device for placement at a predetermined location within a passageway of the human body, and more particularly, relates to a flexible embolization device which may be delivered by a catheter to a pre-selected position within a blood vessel to thereby embolize a blood vessel or a defect in a blood vessel, such as an aneurysm or fistula.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407 to Geremia, et al., entitled, "Method And Apparatus For Placement Of An Embolic Coil" and U.S. Pat. No. 5,122,136to Guglielmi, et al., entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils at predetermined positions within vessels of the human body in order to treat aneurysms, or alternatively, to occlude the blood vessel at a particular location.

Coils, which are placed in vessels, may take the form of helically wound coils, or alternatively, may be random wound coils, coils wound within other coils or other such coil configurations. Examples of various coil configurations are disclosed in U.S. Pat. No. 5,334,210 to Gianturco, entitled, "Vascular Occlusion Assembly" and U.S. Pat. No. 5,382,259 to Phelps, et al., entitled, "Vasoocclusion Coil With Attached Tubular Woven Or Braided Fibrous Coverings." Embolic coils are generally formed of radiopaque material, such as platinum, gold, tungsten or alloys of these metals. Often times several coils are placed at a given location in order to occlude the flow of blood through the vessel by promoting thrombus formation at the particular location.

In the past, embolic coils have been placed within the distal end of a catheter and when the distal end of the catheter is properly positioned the coil may then be pushed out of the end of the catheter with, for example a guidewire, to release the coil at the desired location. This procedure for placement of the embolic coil is conducted under fluoroscopic visualization such that the movement of the coil through the vasculature of the body may be monitored and the coil may be placed in the desired location.

Other embolization devices, such as detachable balloons, are placed in vessels or aneurysms. These balloons usually take the form of an inflatable elastic balloon with a valve assembly for sealing the balloon when a desired inflation is reached. Examples of various detachable balloons are disclosed in U.S. Pat. No. 4,517,979 to Pecenka, entitled, "Detachable Balloon Catheter" and U.S. Pat. No. 4,545,367 to Tucci, entitled, "Detachable Balloon Catheter And Method Of Use." Detachable balloons are generally formed of a flexible polymer and are inflated with a radiopaque solution for visualization under fluoroscopy. Often several balloons are used to fill the aneurysm space. These balloons do not generally conform to the aneurysm space thereby leaving unoccupied space leading to an incomplete aneurysm embolization. Often times a balloon valve may leak thereby causing other balloons to shift position, which may in turn, occlude the parent artery leading to severe complications.

SUMMARY OF THE INVENTION

In accordance with one aspect of the present invention, the vascular embolization system comprises a catheter, a push rod and an embolization device. The embolization device takes the form of an embolization coil surrounded by a foam sleeve. The foam sleeve has a hydrated normal expanded diameter, however it may be compressed and remain compressed when constrained. When the foam sleeve is hydrated and unconstrained, the foam sleeve will return to its normal expanded diameter. The embolization device is positioned in the lumen of the catheter. The push rod is slidably received by the lumen of the catheter and engages the embolization device. Distal movement of the push rod causes the embolization device to exit the lumen of the catheter at a predetermined site within a blood vessel.

In accordance with another aspect of the present invention, there is provided an embolization system comprising an embolization device, which takes the form of an embolization coil, which is impregnated and surrounded by a foam sleeve made of a moldable material. Preferably, the foam sleeve extends into the lumen of the coil.

In another aspect of the present invention there is provided an embolization system, which includes an embolization device having an embolization coil and a foam sleeve bonded to the coil. The embolization device takes the form of a helix. The embolization device is positioned in the lumen of a catheter in a generally straightened configuration, however, upon exiting the distal lumen of the catheter the embolization device returns to the relaxed helical shape. Alternately, the embolization device may take the form of a convoluted shape.

In accordance with another aspect of the present invention there is provided an embolization device that comprises an embolization coil with a foam sleeve disposed about the periphery of the coil. The foam may take the form of a hydrogel and in addition, the embolization device may be used to deliver a therapeutic agent to improve the efficacy of a particular treatment modality. The choice of therapeutic agent depends largely on the particular treatment chosen for a vascular abnormality. In the treatment of an aneurysm the therapeutic agent may be a growth factor such as fibroblast growth factor (FGF) or vascular endothelial growth factor (VEGF) to promote endothelialization and permanent occlusion of the aneurysm. Other therapeutic agents include radioactive materials to aid in the treatment of arteriovenous malformations. Other therapeutic agents include drugs used to obliterate tumors.

In accordance with yet another aspect of the present invention, there is provided an embolization device having an embolization coil and foam sleeve disposed about the coil periphery, which is radiopaque. The embolization device may be made visible under fluoroscopy by using an embolization coil made from a radiopaque material such as a platinum or tungsten alloy. Alternatively, the foam sleeve may be made radiopaque by incorporating a radiopaque filler material such tantalum or tungsten powder or a radiopaque iodine commonly used in contrast media such as RENOGRAFFIN. This radiopaque material aids in the visualization of the embolization device during the medical procedure.

In still another aspect of the present invention there is provided an embolization device that comprises an embolization coil and a foam sleeve bonded to the coil. The embolization coil may contain reinforcing fiber or fibers that are secured in at least two locations and extend through the lumen of the coil to reduce coil stretching. Alternatively, the foam sleeve may contain reinforcing material dispersed throughout the foam, such as long fibers to resist stretching or short fibers or particles to improve sponge mechanical integrity.

In accordance with another aspect of the present invention there is provided an embolization device that comprises an embolization coil surrounded by a foam sleeve. The foam sleeve has a hydrated normal expanded diameter, however, it can be compressed and remain compressed when constrained. When the foam sleeve is hydrated and unconstrained the foam sleeve will return to its normal expanded diameter. Typically, the normal expanded diameter of the foam sleeve is larger than the diameter of the lumen of the catheter.

In accordance with yet another aspect of the present invention there is provided an embolization device that comprises an embolization coil surrounded by a foam sleeve. The foam sleeve has a hydrated normal expanded diameter, however, it can be compressed and remain compressed when constrained. When the foam sleeve is hydrated and unconstrained the foam sleeve will return to its normal expanded diameter. Typically, the normal expanded diameter of the foam sleeve is smaller than the diameter of the catheter used to deliver the embolization device.

In accordance with another aspect of the present invention there is provided a vascular embolization system comprising a push rod, a catheter and an embolization device. The embolization device takes the form of an elongated flexible cylindrical resilient foam. The foam has a normal hydrated expanded diameter and a smaller constrained diameter. When the foam is unconstrained and hydrated the foam returns to the normal expanded diameter. This elongated flexible foam has a length that is at least ten times greater than the normal hydrated diameter.

In another aspect of the present invention there is provided an embolization device, which takes the form of an elongated flexible foam. The foam may take the form of a hydrogel. The foam may be used to deliver therapeutic agents to improve the efficacy of a particular treatment modality.

In yet another aspect of the present invention there is provided an embolization device, which takes the form of an elongated flexible cylindrical foam. To improve the mechanical integrity of the foam, the foam may contain reinforcing materials. Reinforcing materials may take the form of long fiber or fibers incorporated within the foam or short fibers or particles dispersed throughout the foam.

In still another aspect of the present invention there is provided an embolization device, which takes the form of an elongated flexible foam. The foam may be made visible under fluoroscopy by incorporating a radiopaque filler material such tantalum or tungsten powder or a radiopaque iodine commonly used in contrast media such as RENOGRAFFIN. This radiopaque material aids in the visualization of the embolization device during the medical procedure.

In accordance with yet another aspect of the present invention there is provided an embolization system comprising a push rod, a catheter and an embolization device. The embolization device takes the form of an elongated resilient flexible foam having an elongated length that is at least ten times the normal hydrated diameter. The foam takes the shape of a helix. The embolization device is positioned in the lumen of the catheter in a generally straightened configuration. The push rod is slidably disposed into the catheter lumen engaging the embolization device. Distal movement of the push rod causes the embolization device to exit the lumen of the catheter. As the embolization device exits the distal section of the catheter lumen and enters the blood vessel the embolization device returns to its relaxed helical shape. Alternately, in treating a blood vessel defect such as an aneurysm, the embolization may have a preferred convoluted shape.

In accordance with another aspect of the present invention there is provided an embolization system comprising a push rod, a catheter and an embolization device. The embolization device takes the form of an elongated flexible resilient cylindrical foam. The foam has a normal expanded diameter when hydrated and a smaller compressed diameter when constrained. The normal expanded diameter of the foam may be larger than the diameter of the lumen of the catheter.

In accordance with another aspect of the present invention there is provided an embolization system comprising a push rod, a catheter and an embolization device. The embolization device takes the form of an elongated flexible resilient cylindrical foam. The foam has a normal expanded diameter when hydrated and a smaller compressed diameter when constrained. The normal expanded diameter of the foam material may be smaller than the diameter of the catheter used to deliver the embolization device.

In accordance with yet another aspect of the present invention there is provided a vascular embolization system comprising a push rod, a catheter and an embolization device. The embolization device includes a flexible wire and a resilient foam sleeve disposed about the wire. The foam sleeve has a normal hydrated expanded diameter and a smaller constrained diameter such that when unconstrained and hydrated said foam sleeve returns to the normal expanded diameter.

DESCRIPTION OF THE PREFERRED EMBODIMENT

Figure 1:
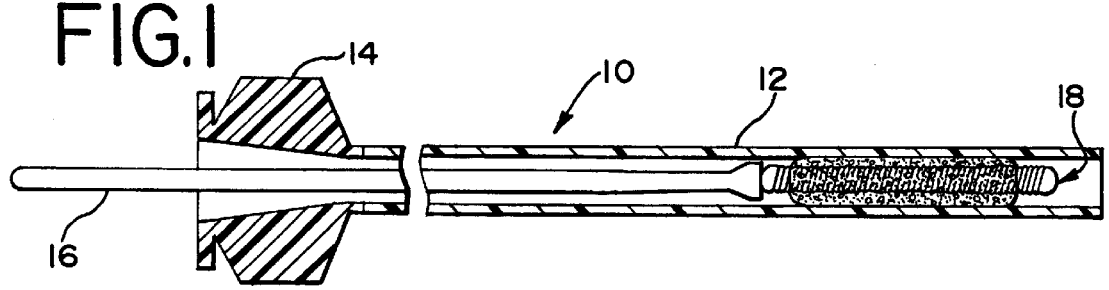
FIG. 1 illustrates a partial section view of a first embodiment of the vascular embolization system of the present invention.

FIG. 1 illustrates a first embodiment of the vascular embolization system 10. The vascular embolization system 10 includes a catheter 12, having a proximal hub 14, push rod 16 and embolization device 18. Embolization device 18 is disposed within the lumen at the distal section of catheter 12. Push rod 16 is slidably disposed within the lumen of catheter 12, proximal to embolization device 18.

Figure 2A:
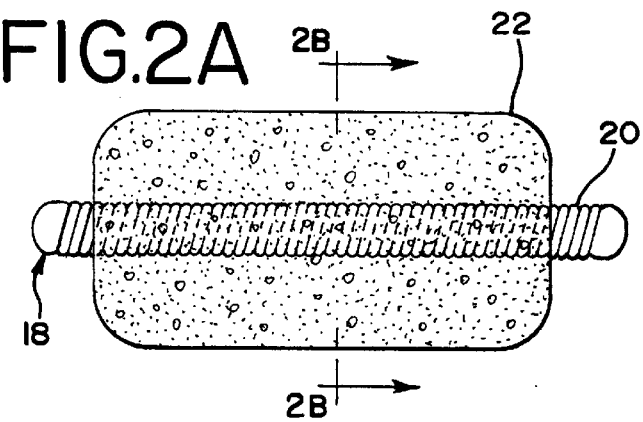
FIG. 2A illustrates an axial view of an embolization device according to the present invention.
Figure 2B:
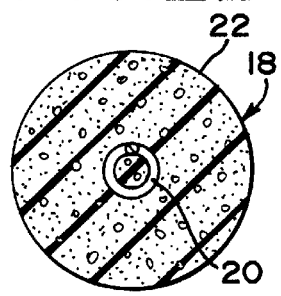
FIG. 2B illustrates a cross sectional view of the embolization device depicted in FIG. 2A.

FIGS. 2A and 2B show axial and cross sectional views of embolization device 18. The embolization device 18 comprises an embolization coil 20 surrounded by a foam sleeve 22. The embolization coil 20 is of the type commonly used to reduce or embolize a particular blood vessel. Depending on the flexibility needed and catheter system utilized the embolization coil 20 ranges in diameter from about 0.002 inches to 0.150 inches with a preferred range of about 0.006 inches to 0.052 inches. Materials used to make the embolization coil 20 include polymers, metals or composites in filament form. A wide variety of polymers are suitable for the embolization coil such as nylons, polyesters, collagen, polyvinylalcohol or hydrogels of polyvinylalcohol or polyvinylpyrrolidone. Metals are often used to form embolization coils that are biocompatible and provide the desired flexibility like platinum, gold and nickel-titanium alloys. The preferred material being metals formed of platinum alloys. The foam sleeve 22 is a foam material that is secured using thermal, adhesive or mechanical means to the embolization coil 20. As shown in FIG. 2B, embolization device 18 is illustrated in cross section. The foam sleeve 22 is formed of a biocompatible material. Foams for use in the preferred embodiment and alternate embodiments are generally polymeric in nature and can be formed of many materials such as collagen, polyvinylalcohol (PVA), polyvinylpyrrolidone (PVP), polyurethane or polyetherpolycarbonate. In the preferred embodiment, foam sleeve 22 is molded about coil 20 using liquid components that when reacted form a solid flexible foam, such as those described in U.S. Pat. No. 4,550,126. Preferably the foam material extends within the lumen of coil 20. To improve the integrity and mechanical properties of these foams reinforcing materials can be incorporated into the foam. Typically reinforcing material is in the form of high strength flexible fibers, however particles are also acceptable. These foams generally have a hydrated normal expanded diameter and a smaller compressed diameter when constrained. These foams are flexible and resilient, such that when unconstrained and sufficiently hydrated they return to the normal expanded diameter. The diameter of any of the foams of the preferred embodiment are largely dependent on the catheter used and the vasculature to be occluded, but generally is in the range of about 0.01 mm to 20 mm preferably in the range of about 0.1 mm to 5 mm. The structure of the foams, such as in foam sleeve 22 can be that of open celled, closed celled or a combination of both however, preferably open celled. To improve the visibility of the foams under fluoroscopy, radiopaque materials such as platinum, tungsten, tantalum, gold, barium or iodine can be incorporated within or bonded to the foam. As can be appreciated these foams can be comprised of biocompatible hydrogel materials, such as PVA, PVP, collagen, etc., making them suitable for delivery of therapeutic agents. These therapeutic agents can include radioactive particles to deliver therapeutic radiation, growth factors such as VEGF or FGF, chemotherapy agents as well as other drugs to treat tumors.

Figure 3:
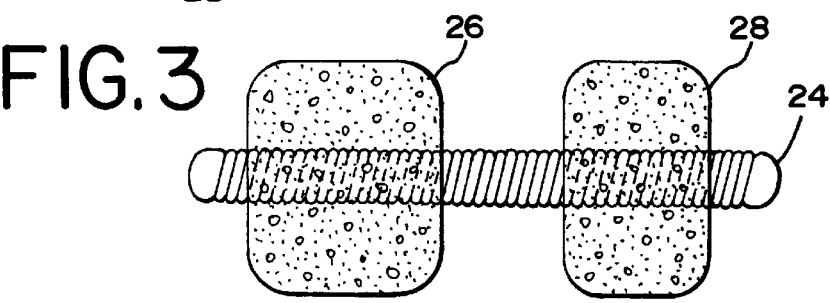
FIG. 3 illustrates an alternative embodiment of an embolization device according to the present invention.
Figure 4:
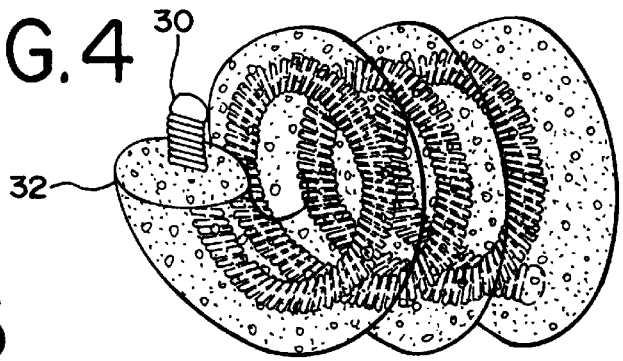
FIG. 4 illustrates another alternative embodiment of an embolization device having a helical shape according to the present invention.

FIGS. 3 and 4 illustrate alternate embodiments of the present invention. In a first alternate preferred embodiment depicted in FIG. 3, foam sleeve elements 26 and 28 are disposed about coil 24. The foam sleeve elements 26 and 28 are formed onto the coil 24 using aforementioned materials and methods. As can be appreciated, only their length and the length of the coil limit the number of foam sleeve elements. The foam sleeve elements 26 and 28 generally have a cylindrical shape. A variation of the first alternate preferred embodiment includes foam sleeve elements disposed about the coil, in which the length of one foam sleeve element extends far distal from the end of the coil. The length the foam element that extends from the end of the coil is in the range of 10 to 500 times the length of the coil with a preferred range of about 20 to 300 times the coil length. In a second alternate preferred embodiment shown in FIG. 4, foam sleeve 32 is disposed about coil 30. Coil 30 is formed into a helical shape and consequentially foam sleeve 32 also takes this helical shape. Alternatively coil 30 could be of a straight configuration, placed in a helical mold and foam sleeve 32 molded about coil 30 in a helical shape. As can be appreciated the coil 30 can be shaped complex, convoluted, spherical, conical, spiral or any other shape that is suitable for occluding the blood vessel or vascular malformation.

Figure 5:
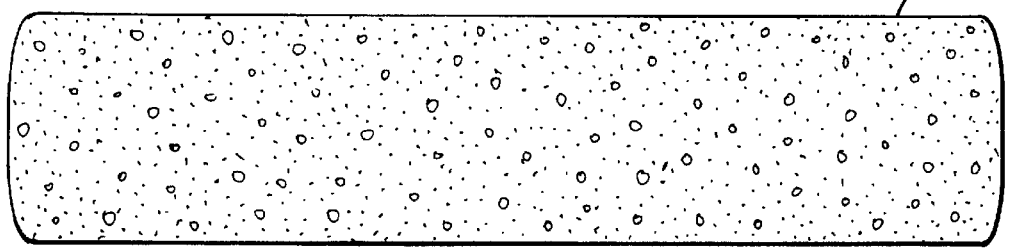
FIG. 5 illustrates yet another alternative embodiment of an elongated embolization device according to the present invention.

FIG. 5 illustrates a third alternate preferred embodiment in which the embolization device of the vascular embolization system is an elongated foam material 34. The elongated foam material 34 of the present invention is open celled, however variations could include closed cells or a combination of both. The elongated foam material 34 generally has a primary long cylindrical shape. As can be appreciated, this long cylindrical shape can have a secondary shape that is helical, conical, spherical, complex or convoluted pertinent shape to aid in delivery or occlusion. The length of the elongated foam material 34 is at least ten times its primary diameter but preferably greater than fifteen times the primary diameter.

Figure 6A:
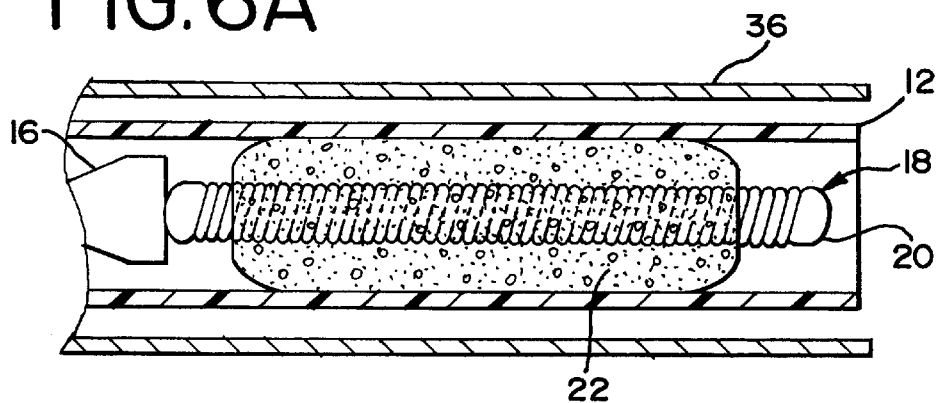
FIGS. 6A through 6C illustrate a sequence of delivery and deployment of an embolization device in a vessel according to the present invention.
Figure 6B:
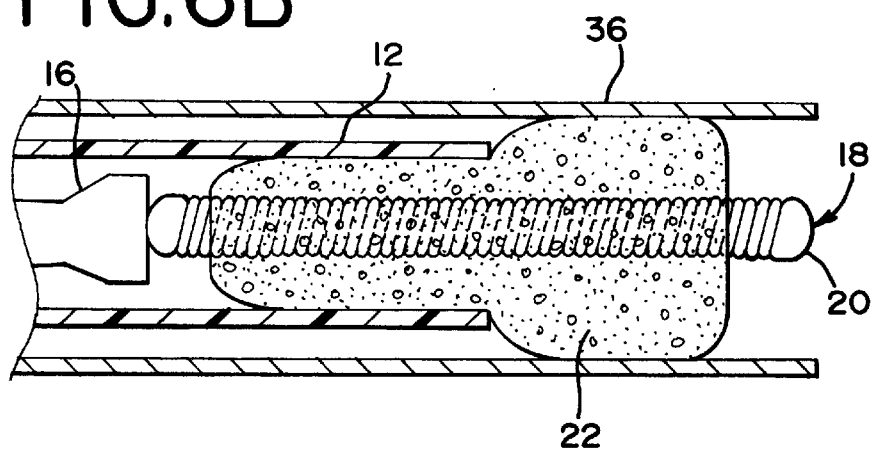
Figure 6C:
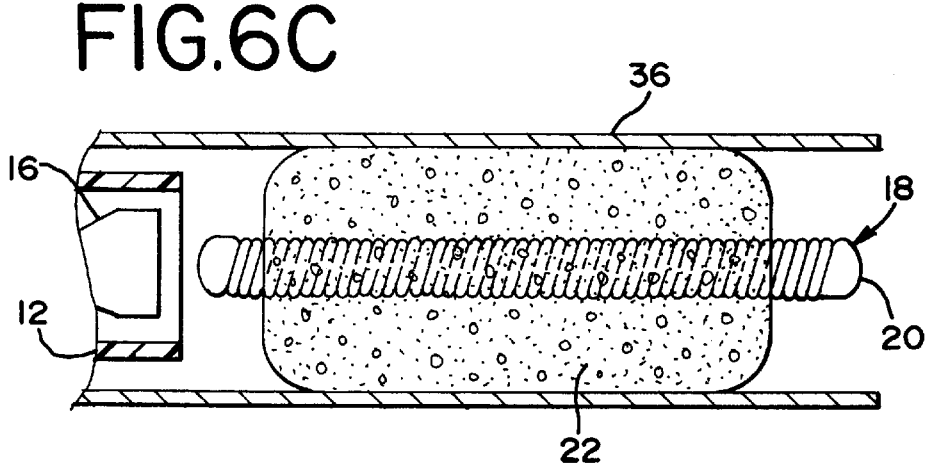

FIGS. 6A, 6B and 6C illustrate the sequence of positioning and deploying the vascular embolization system 10 within a blood vessel. FIG. 6A depicts catheter 12 properly positioned within a blood vessel 36 selected for embolization. Push rod 16 and embolization device 18 are introduced into the lumen of catheter 12. Distal movement of push rod 16 advances embolization device 18 to the distal section of catheter 12. Further distal movement of push rod 16 causes embolization device 18 to exit the lumen of catheter 12. As shown in FIGS. 6B and 6C, the embolization device 18 exits the lumen of catheter 12 and the foam sleeve 22 expands. The foam sleeve 22 expands to its hydrated normal expanded diameter within the vessel and thereby embolizes the vessel.

As can be appreciated, numerous variations of the present invention exist to treat the limitless variations in blood vessel and vascular malformation anatomy. It is within the scope of the present invention to use various known detachable positioning mechanisms to deploy the vascular embolization device of the present invention.

That which is claimed is:

1. A vascular embolization system for treating a defect in a blood vessel comprising:

a catheter having a proximal section, a distal section and an outer wall defining a lumen therethrough;

a push rod slidably disposed within the lumen of said catheter having a proximal end and a distal end; and, an embolization device comprising an elongated coil having a lumen and a cylindrical foam sleeve disposed about said coil and extending into the lumen of the coil, said cylindrical foam sleeve having a hydrated normal expanded diameter and a smaller constrained diameter such that when unconstrained and hydrated said cylindrical foam sleeve returns to the normal expanded diameter;

said embolization device being disposed within the lumen at the distal section of said catheter, the distal end of the push rod engages the embolization device such that distal movement of the push rod causes the embolization device to exit the lumen of the catheter at a pre-selected position within the blood vessel.

2. A vascular embolization system as defined in claim 1, wherein said embolization device takes a convoluted shape.

3. A vascular embolization system as defined in claim 1, wherein said embolization device is comprised of a radiopaque material.

4. A vascular embolization system as defined in claim 1, wherein said embolization device is comprised of a therapeutic agent.

5. A vascular embolization system as defined in claim 1, wherein said cylindrical foam sleeve has a larger normal expanded diameter than a diameter of the lumen of said catheter.

6. A vascular embolization system as defined in claim 1, wherein said cylindrical foam sleeve has smaller normal expanded diameter than an outer diameter of said catheter.

7. A vascular embolization system as defined in claim 1, wherein said embolization device takes the shape of a helix.

8. A vascular embolization system as defined in claim 7, wherein said cylindrical foam sleeve is a moldable foam material that is bonded to the coil.

9. A vascular embolization system as defined in claim 8, wherein said coil comprises a lumen and said cylindrical foam sleeve is impregnated in said coil.

10. A vascular embolization system as defined in claim 9, wherein said cylindrical foam sleeve is a hydrogel.

11. A vascular embolization system as defined in claim 10, wherein said embolization device includes a reinforcing material.

12. A vascular embolization system as defined in claim 11, wherein said reinforcing material is at least one fiber.

13. A vascular embolization system for treating a defect in a blood vessel comprising:
    a catheter having a proximal section, a distal section and an outer wall defining a lumen therethrough;
    a push rod slidably disposed within the lumen of said catheter having a proximal end and a distal end; and,
    an embolization device comprising a flexible wire having a lumen and a foam sleeve disposed about said wire and extending into the lumen of the wire, said foam sleeve having a hydrated normal expanded diameter and a smaller constrained diameter such that when unconstrained and hydrated said foam sleeve returns to the normal expanded diameter;
    said embolization device being disposed within the lumen at the distal section of said catheter, the distal end of the push rod engages the embolization device such that distal movement of the push rod causes the embolization device to exit the lumen of the catheter at a pre-selected position within the blood vessel.

14. A vascular embolization system as defined in claim 13, wherein said embolization device takes the shape of a helix.

15. A vascular embolization system as defined in claim 13, wherein said embolization device takes a convoluted shape.

16. A vascular embolization system as defined in claim 13, wherein said embolization device includes a radiopaque material.

17. A vascular embolization system as defined in claim 13, wherein said embolization device includes a therapeutic agent.

18. A vascular embolization system as defined in claim 13, wherein said foam sleeve has a larger normal hydrated diameter than a diameter of the lumen of said catheter.

19. A vascular embolization system as defined in claim 13, wherein said foam sleeve has a smaller normal expanded diameter than an outer diameter of said catheter.

20. A vascular embolization system as defined in claim 13, wherein said foam sleeve is a hydrogel.

21. A vascular embolization system as defined in claim 20, wherein said embolization device includes a reinforcing material.

22. A vascular embolization system as defined in claim 21, wherein said reinforcing material is at least one fiber.

23. A vascular embolization device for treating a defect in a blood vessel comprising:
    an elongated coil having a lumen and a cylindrical foam sleeve disposed about said coil and extending into the lumen of the coil, said cylindrical foam sleeve having a hydrated normal expanded diameter and a smaller constrained diameter such that when unconstrained and hydrated said cylindrical foam sleeve returns to the normal expanded diameter.

24. A vascular embolization device as defined in claim 23, wherein said elongated coil takes a convoluted shape.

25. A vascular embolization device as defined in claim 23, wherein said cylindrical foam sleeve is comprised of a radiopaque material.

26. A vascular embolization device as defined in claim 23, wherein said cylindrical foam sleeve is comprised of a therapeutic agent.

27. A vascular embolization device as defined in claim 23, wherein said elongated coil takes the shape of a helix.

28. A vascular embolization device as defined in claim 27, wherein said cylindrical foam sleeve is a moldable foam material that is bonded to the elongated coil.

29. A vascular embolization device as defined in claim 28, wherein said elongated coil comprises a lumen and said cylindrical foam sleeve is impregnated in said elongated coil.

30. A vascular embolization device as defined in claim 29, wherein said cylindrical foam sleeve is a hydrogel.

31. A vascular embolization device as defined in claim 30, wherein said cylindrical foam sleeve includes a reinforcing material.

32. A vascular embolization device as defined in claim 31, wherein said reinforcing material is at least one fiber.

33. A vascular embolization device for treating a defect in a blood vessel comprising:
    a flexible wire having a lumen and a foam sleeve disposed about said wire and extending into the lumen of the wire, said foam sleeve having a hydrated normal expanded diameter and a smaller constrained diameter such that when unconstrained and hydrated said foam sleeve returns to the normal expanded diameter.

34. A vascular embolization device as defined in claim 33, wherein said flexible wire takes the shape of a helix.

35. A vascular embolization device as defined in claim 33, wherein said flexible wire takes a convoluted shape.

36. A vascular embolization device as defined in claim 33, wherein said foam sleeve includes a radiopaque material.

37. A vascular embolization device as defined in claim 33, wherein said foam sleeve includes a therapeutic agent.

38. A vascular embolization device as defined in claim 33, wherein said foam sleeve is a hydrogel.

39. A vascular embolization device as defined in claim 38, wherein said foam sleeve includes a reinforcing material.

40. A vascular embolization device as defined in claim 39, wherein said reinforcing material is at least one fiber.

41. A vascular embolization system for treating a defect in a blood vessel comprising:
    a catheter having a proximal section, a distal section and an outer wall defining a lumen therethrough;
    a push rod slidably disposed within the lumen of said catheter having a proximal end and a distal end; and, an embolization device comprising an elongated coil having a lumen and a cylindrical foam sleeve disposed about said coil and extending into the lumen of the coil, said cylindrical foam sleeve having a normal expanded diameter and a smaller constrained diameter such that when unconstrained said cylindrical foam sleeve returns to the normal expanded diameter;

said embolization device being disposed within the lumen at the distal section of said catheter, the distal end of the push rod engages the embolization device such that distal movement of the push rod causes the embolization device to exit the lumen of the catheter at a pre-selected position within the blood vessel.

42. A vascular embolization system for treating a defect in a blood vessel comprising:

a catheter having a proximal section, a distal section and an outer wall defining a lumen therethrough;

a push rod slidably disposed within the lumen of said catheter having a proximal end and a distal end; and, sleeve an embolization device comprising a flexible wire having a lumen and a foam sleeve disposed about said wire and extending into the lumen of the wire, said foam sleeve having a normal expanded diameter and a smaller constrained diameter such that when unconstrained said foam sleeve returns to the normal expanded diameter;

said embolization device being disposed within the lumen at the distal section of said catheter, the distal end of the push rod engages the embolization device such that distal movement of the push rod causes the embolization device to exit the lumen of the catheter at a pre-selected position within the blood vessel.

* * * * *

UNITED STATES PATENT AND TRADEMARK OFFICE
CERTIFICATE OF CORRECTION

PATENT NO. : 6,723,108 B1
DATED : April 20, 2004
INVENTOR(S) : Donald K. Jones and Vladimir Mitelberg It is certified that error appears in the above-identified patent and that said Letters Patent is hereby corrected as shown below:

Column 10,
Line 3, "sleeve an embolization device comprising a flexible wire" should read:
-- an embolization device comprising a flexible wire --

Signed and Sealed this

Thirty-first Day of August, 2004

JON W. DUDAS
*Director of the United States Patent and Trademark Office*